United States Patent
Tanba et al.

(10) Patent No.: US 11,504,697 B2
(45) Date of Patent: Nov. 22, 2022

(54) POROUS CARBON MATERIAL, METHOD FOR PRODUCING SAME, AND SYNTHESIS REACTION CATALYST

(71) Applicant: Dexerials Corporation, Tokyo (JP)

(72) Inventors: Katsuya Tanba, Tokyo (JP); Yoshiharu Okuda, Tokyo (JP); Teiko Kuroda, Tokyo (JP)

(73) Assignee: Dexerials Corporation, Tokyo (JP)

( * ) Notice: Subject to any disclaimer, the term of this patent is extended or adjusted under 35 U.S.C. 154(b) by 77 days.

(21) Appl. No.: 16/335,340

(22) PCT Filed: Sep. 12, 2017

(86) PCT No.: PCT/JP2017/032942
§ 371 (c)(1),
(2) Date: Mar. 21, 2019

(87) PCT Pub. No.: WO2018/056126
PCT Pub. Date: Mar. 29, 2018

(65) Prior Publication Data
US 2019/0275498 A1    Sep. 12, 2019

(30) Foreign Application Priority Data

Sep. 26, 2016    (JP) .............................. JP2016-187106

(51) Int. Cl.
*B01J 21/18* (2006.01)
*C01B 32/324* (2017.01)
(Continued)

(52) U.S. Cl.
CPC ............... *B01J 21/18* (2013.01); *B01J 23/44* (2013.01); *B01J 35/10* (2013.01); *B01J 35/1023* (2013.01);
(Continued)

(58) Field of Classification Search
None
See application file for complete search history.

(56) References Cited

U.S. PATENT DOCUMENTS 5,242,879 A    9/1993    Abe et al.
6,066,589 A    5/2000    Malentacchi et al.
(Continued)

FOREIGN PATENT DOCUMENTS

CN    105122540    12/2015
JP    10-000355    1/1998
(Continued)

OTHER PUBLICATIONS

Muniandy et al.; The Synthesis and Characterization of high Purity Mixed Microporous/Mesoporous Activated Carbon from Rice Husk Using Chemical Activation with NaOH and KOH; Microporous and Mesoporous Materials; 107, 316-323; 2014.*

(Continued)

*Primary Examiner* — Guinever S Gregorio
(74) *Attorney, Agent, or Firm* — CarmodyTorrance Sandak & Hennessey LLP

(57) ABSTRACT

A porous carbon material,
wherein a half width (2θ) of a diffraction peak (10x) (38° to 49°) by X-ray diffraction is 4.2° or less, and
wherein a ratio (mesopore volume/micropore volume) of a mesopore volume ($cm^3/g$) measured by a BJH method to a micropore volume ($cm^3/g$) measured by a HK method is 1.20 or more.

16 Claims, 3 Drawing Sheets

(51) Int. Cl.
| | |
|---|---|
| C01B 32/372 | (2017.01) |
| B01J 23/44 | (2006.01) |
| B01J 35/10 | (2006.01) |
| B01J 37/02 | (2006.01) |
| B01J 37/18 | (2006.01) |
| C07C 5/08 | (2006.01) |
| C07C 15/18 | (2006.01) |
| B01J 37/08 | (2006.01) |
| C01B 32/30 | (2017.01) |
| C07B 61/00 | (2006.01) |

(52) U.S. Cl.
 CPC ....... *B01J 35/1028* (2013.01); *B01J 35/1038* (2013.01); *B01J 35/1042* (2013.01); *B01J 35/1047* (2013.01); *B01J 37/0215* (2013.01); *B01J 37/0236* (2013.01); *B01J 37/08* (2013.01); *B01J 37/18* (2013.01); *C01B 32/30* (2017.08); *C01B 32/324* (2017.08); *C01B 32/372* (2017.08); *C07C 5/08* (2013.01); *C07C 15/18* (2013.01); *C01P 2002/72* (2013.01); *C01P 2006/12* (2013.01); *C01P 2006/14* (2013.01); *C07B 61/00* (2013.01)

(56) References Cited

U.S. PATENT DOCUMENTS

| | | |
|---|---|---|
| 2010/0291167 A1 | 11/2010 | Iida et al. |
| 2015/0357637 A1 | 12/2015 | Yamanoi et al. |
| 2016/0028135 A1 | 1/2016 | Iida et al. |

FOREIGN PATENT DOCUMENTS

| | | |
|---|---|---|
| JP | 11-90223 | 4/1999 |
| JP | 2008-290062 | 12/2008 |
| JP | 2010100516 | 5/2010 |
| JP | 2015-164889 | 9/2015 |
| JP | 2016-028014 | 2/2016 |
| KR | 19940010111 | 10/1994 |
| TW | 470667 | 1/2002 |
| WO | 2014112401 | 7/2014 |

OTHER PUBLICATIONS

Google Translation Ito et al. JP 2015164889; Jun. 4, 2022.*
Japanese Patent Determination Gazette issued in corresponding Japanese Application No. 2019-700538 dated Oct. 30, 2020.
Shinji Ishikawa et al., "Carbon Materials with Nano-sized Pores Derived from Carbides", SEI technical review, Jan. 2016, vol. 188, pp. 139-144 (Partial Translation).
Tsutomu Suzuki et al., "Production of Functional Carbon by Iron-Catalyzed Carbonization of Biomass-Effect of Washing with Acid Followed by Atmospheric Oxidation on the Electroconductivity of Crystallized Mesoporous Wood Carbon", Transactions of the Materials Research Society of Japan, 2011, vol. 36, No. 3, p. 417-420.
Japanese Industrial Standards "Pore Size Distribution and Porosity of Solid Materials—Part 3: Analysis of Micropores by Gas Adsorption" JIS Z 8831-3:2010 (Partial Translation).
Japanese Industrial Standards "Pore Size Distribution and Porosity of Solid Materials—Part 2: Analysis of Mesopores and Macropores by Gas Adsorption" JIS Z 8831-2:2010 (Partial Translation).
Extended European Search Report dated Apr. 3, 2020 issued for corresponding EP application No. 17852903.8.
Muniandy, L. et al., "The synthesis and characterization of high purity mixed microporous/mesoporous activated carbon from rice husk using chemical activation with NaOH and KOH", Microporous and Mesoporous Materials, vol. 197, Jun. 28, 2014, pp. 316-323.
Kim, Y. et al., "Complete degradation of perchlorate using Pd/N-doped activated carbon with adsorption/catalysis bifunctional roles", Carbon, vol. 65, Aug. 26, 2013, pp. 315-323.
Kania, N. et al., "Scope and limitation of activated carbons in aqueous organometallic catalysis", Journal of Catalysis, vol. 278, No. 2, Dec. 7, 2010, pp. 208-218.
Taiwanese Patent Office, Office Action issued in corresponding Taiwanese Application No. 106132322, dated Feb. 4, 2021.
Japanese Patent Determination Gazette issued in corresponding Objection No. 2019-700538 dated Oct. 30, 2020.
The Patent Office of the People's Republic of China, Chinese Notification of Office Action issued for corresponding Chinese Patent Application No. 201780058526.7, dated Oct. 29, 2021.
Korean Patent Office, Office Action issued in corresponding Korean Patent Application No. 10-2019-7011091 dated Aug. 27, 2021.

* cited by examiner

POROUS CARBON MATERIAL, METHOD FOR PRODUCING SAME, AND SYNTHESIS REACTION CATALYST

TECHNICAL FIELD

The present invention relates to a porous carbon material, and a method for producing the porous carbon material, and a synthesis reaction catalyst.

BACKGROUND ART

Porous carbon materials represented by activated carbon are obtained by activating charred products, which are made from plant materials (e.g., wood pulp, coconut shell, and chaff), mineral materials (e.g., coal, tar, and petroleum pitch), and synthetic resins, through treatment with gases or chemicals under a high temperature to thereby form fine pores. The fine pores form a network structure within carbon and result in a large surface area. Therefore, the porous carbon material is excellent in an adsorption ability. As a result, the porous carbon material has been widely used in a variety of applications such as odor removal, impurity removal in liquid, and solvent vapor recovery or removal.

In addition to such applications, the porous carbon materials are also used as carriers in catalysts. Heterogeneous catalysts can be obtained by allowing metals or metal compounds to be carried on the porous carbon materials. For example, activated carbon carrying metals or metal compounds is used as a catalyst for the synthesis of vinyl acetate and vinyl chloride.

Regarding catalyst carriers which are porous carbon materials, for example, a catalyst carrier made of a carbon material produced by heating activated carbon having a specific surface area of 1,700 $m^2/g$ or more at 1,600° C. to 2,500° C. is used as a catalyst carrier for a fuel cell electrode (see PTL 1). It has also been proposed to use a catalyst for an electrode of a fuel cell, in which a catalytic active component such as platinum or a platinum alloy is carried on this catalyst carrier.

CITATION LIST

Patent Literature

PTL 1 Japanese Patent Application Laid-Open (JP-A) No. 2008-290062

SUMMARY OF INVENTION

Technical Problem

The present invention aims to achieve the following object.

That is, an object of the present invention is to provide a porous carbon material useful as a catalyst carrier, and a method for producing the porous carbon material, and a synthesis reaction catalyst using the porous carbon material.

Solution to Problem

Means for achieving the above object are as follows.
<1> A porous carbon material,
 wherein a half width (2θ) of a diffraction peak (10x) (38° to 49°) by X-ray diffraction is 4.2° or less, and
 wherein a ratio (mesopore volume/micropore volume) of a mesopore volume ($cm^3/g$) measured by a BJH method to a micropore volume ($cm^3/g$) measured by a HK method is 1.20 or more.
<2> The porous carbon material according to <1>, wherein the porous carbon material is derived from a plant.
<3> The porous carbon material according to <1> or <2>, wherein the porous carbon material is derived from chaff.
<4> The porous carbon material according to any one of <1> to <3>, wherein the porous carbon material is a carrier for a catalyst.
<5> A method for producing the porous carbon material according to any one of <1> to <4>, the method including:
 removing, from a raw material containing a silicon component, the silicon component by an acid treatment or an alkali treatment, and then performing a carbonization treatment.
<6> The method for producing the porous carbon material according to <5>, wherein an activation treatment is performed after the carbonization treatment.
<7> A method for producing the porous carbon material according to any one of <1> to <4>, the method including:
 performing a carbonization treatment on a raw material containing a silicon component, then removing the silicon component from an obtained carbonized product by an acid treatment or an alkali treatment, and then performing an activation treatment.
<8> The method for producing the porous carbon material according to <6> or <7>, wherein a heat treatment is performed after the activation treatment.
<9> The method for producing the porous carbon material according to <8>, wherein a temperature of the heat treatment is 1,200° C. or higher.
<10> The method for producing the porous carbon material according to any one of <5> to <9>, wherein a temperature of the carbonization treatment is 600° C. or higher.
<11> A synthesis reaction catalyst including:
 the porous carbon material according to any one of <1> to <4>; and
 a metal or a metal compound carried on the porous carbon material.
<12> The synthesis reaction catalyst according to <11>, wherein the metal or the metal compound is palladium.

Advantageous Effects of Invention

According to the present invention, it is possible to achieve the above object, and provide a porous carbon material useful as a catalyst carrier, and a method for producing the porous carbon material, and a synthesis reaction catalyst using the porous carbon material.

DESCRIPTION OF EMBODIMENTS (Porous Carbon Material)

Figure 1:
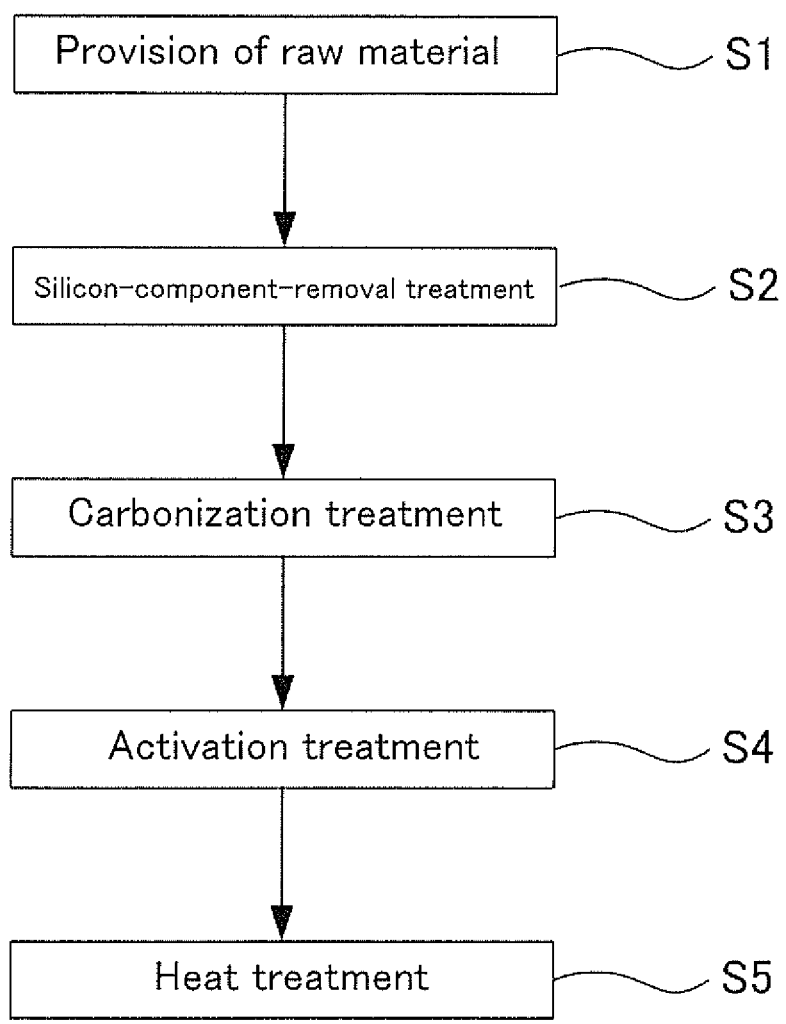
FIG. 1 is a flowchart of one example of a method for producing a porous carbon material.

A porous carbon material of the present invention meets the following (1) and (2):
(1) a half width (2θ) of a diffraction peak (10x) (38° to 49°) by X-ray diffraction is 4.2° or less; and
(2) a ratio (mesopore volume/micropore volume) of a mesopore volume ($cm^3/g$) measured by a BJH method to a micropore volume ($cm^3/g$) measured by a HK method is 1.20 or more.

The present inventors conducted extensive studies to provide a porous carbon material useful as a carrier of a catalyst capable of efficiently performing a chemical reaction.

As a result, the present inventors have found that when a porous carbon material meets both of the (1) and (2) above, the porous carbon material is useful as a carrier of a catalyst capable of efficiently performing a chemical reaction (in particular, a hydrogenation reduction reaction). On the basis of this finding, the present inventors have completed the present invention.

The present inventors believe the following as one possible reason why when a porous carbon material meets both of the (1) and (2) above, the porous carbon material is useful as a carrier of a catalyst capable of efficiently performing a chemical reaction (in particular, a hydrogenation reduction reaction).

Specifically, efficiency of chemical reactions and reaction yield are greatly influenced by electrical conductivity and pore distribution of a catalyst carrying a metal element or the like on a porous carbon material. That is, the flow of electrons in a catalyst carrier becomes faster when the electrical conductivity of the porous carbon material is high, and thus the carried metal or metal compound is reused at a higher rate, leading to increased reactivity.

The diffraction peak (10x) (38° to 49°) by X-ray diffraction is considered to be a peak of pseudo graphite appearing when the carbon density is increased. When the half width (2θ) is 4.2° or less, the electrical conductivity is increased and the flow of electrons in a catalyst carrier becomes faster. Thus, the carried metal or metal compound is reused at a higher rate, leading to increased reactivity. The half width is expected to represent a specific resistance value of a material.

In addition, when the mesopore volume becomes relatively large (in other words, the micropore volume becomes relatively small) in the porous carbon material, the porous carbon material exhibits an effect as a carrier of a heterogeneous catalyst. Specifically, catalytic particles such as metals and metal compounds carried on the porous carbon material are generally as small as 5 nm or less, and thus they enter the micropores and those entered metal catalyst particles do not contribute to activity. Therefore, carriers having a relatively large mesopore volume and a relatively small micropore volume are considered to be effective as a catalyst application.

Therefore, when both of the (1) and (2) above are met, it is possible to obtain a porous carbon material useful as a carrier of a catalyst capable of efficiently performing a chemical reaction (in particular, a hydrogenation reduction reaction).

<Half Width>

In the porous carbon material, a half width (2θ) of a diffraction peak (10x) (38° to 49°) by X-ray diffraction is 4.2° or less, preferably 4.0° or less. The upper limit of the half width is not particularly limited and may be appropriately selected depending on the intended purpose. The half width (2θ) is preferably 3.0° or more, more preferably 3.5° or more.

Here, "10x" means a pseudo peak observed in the vicinity of the 101 plane in graphite.

The X-ray diffraction measurement and the measurement of the half width can be performed by a known X-ray diffractometer, for example, PHILIPS X'Pert available from PANalytical Co.

An exemplary method of adjusting the half width (2θ) to be 4.2° or less is a method of heat treating a porous carbon material. Such a heat treatment will be described below.

<Pore Volume>

The porous carbon material has many pores. The pores are classified into mesopores, micropores, and macropores. As used herein, the mesopores refer to pores having a pore diameter of 2 nm to 50 nm, the micropores refer to pores having a pore diameter of less than 2 nm, and the macropores refer to pores having a pore diameter of more than 50 nm.

In the porous carbon material, a ratio (mesopore volume/micropore volume) of a mesopore volume ($cm^3/g$) to a micropore volume ($cm^3/g$) is 1.20 or more, preferably 1.30 or more. The upper limit of the ratio is not particularly limited and may be appropriately selected depending on the intended purpose. The ratio is preferably 5.00 or less, more preferably 2.00 or less.

<<Mesopore Volume>>

The mesopore volume is not particularly limited and may be appropriately selected depending on the intended purpose. The mesopore volume is preferably 0.20 $cm^3/g$ or more but 1.50 $cm^3/g$ or less, more preferably 0.30 $cm^3/g$ or more but 1.30 $cm^3/g$ or less, particularly preferably 0.40 $cm^3/g$ or more but 1.20 $cm^3/g$ or less. When the mesopore volume is less than 0.20 $cm^3/g$, the ratio of 1.20 or more is difficult to achieve.

The mesopore volume can be measured using, for example, the device described below.

The mesopore volume can be determined by measuring a nitrogen adsorption isotherm using 3Flex available from Micromeritics Japan LLC and calculating the mesopore volume using the BJH method.

The BJH method is a widely used method as a pore distribution analysis method. When a pore distribution is analyzed based on the BJH method, nitrogen serving as adsorbing molecules is adsorbed on and desorbed from a porous carbon material to determine a desorption isotherm. Then, based on the desorption isotherm, a thickness of an adsorption layer while the adsorbing molecules (e.g., nitrogen) are desorbed stepwise from a state in which pores are filled with the adsorbing molecules and an inner diameter of pores generated thereupon (twice as long as a core radius). A pore radius $r_p$ is calculated based on the following expression (1) and a pore volume is calculated based on the following expression (2). Then, based on the pore radius and the pore volume, rates of change in pore volume are plotted against pore diameters ($2r_p$) ($dV_p/dr_p$) to thereby generate a pore distribution curve (see, a manual of BELSORP-mini and BELSORP analysis software (available from Microtrac-BEL Corp.), pages 85 to 88).

$$r_p = t + r_k \quad (1)$$

$$V_{pn} = R_n \cdot dV_n - R_n \cdot dt_n \cdot c \cdot \Sigma A_{pj} \quad (2)$$

$$\text{wherein } R_n = r_{pn}^2/(r_{kn-1} + dt_n)^2 \quad (3)$$

In the above expressions, $r_p$: pore radius;

$r_k$: core radius (inner diameter/2) when an adsorption layer having a thickness t is adsorbed on an inner wall of a pore having the pore radius $r_p$ at the pressure;

$V_{pn}$: pore volume when nitrogen is desorbed at the n th time;

$dV_n$: amount of change at that time;

$dt_n$: amount of change in thickness to of the adsorption layer when nitrogen is desorbed at the n th time;

$r_{kn}$: core radius at that time;

c: constant value; and $r_{pn}$: pore radius when nitrogen is desorbed at the n th time.

Also, $\Sigma A_{pj}$ represents an integrated value of a wall surface area of the pore in a range of from j=1 to j=n−1.

<<Micropore Volume>>

The micropore volume is not particularly limited and may be appropriately selected depending on the intended purpose. The micropore volume is preferably 0.15 cm³/g or more but 1.00 cm³/g or less, more preferably 0.20 cm³/g or more but 0.90 cm³/g or less, particularly preferably 0.30 cm³/g or more but 0.80 cm³/g or less. When the micropore volume is too large, the ratio of 1.20 or more is difficult to achieve.

The micropore volume can be measured using, for example, the device described below.

Specifically, the micropore volume can be calculated by the HK method by measuring a nitrogen adsorption isotherm using 3Flex available from Micromeritics Japan LLC.

The HK method is an abbreviation of "Horvath-Kawazoe's method". This method assumes that the pores are in the form of slits. By expressing the adsorption energy to the pores by the distance between the slit wall surface and the adsorbed molecule, the adsorption energy can also be thermodynamically expressed from the adsorption molecular weight, so that the relationship between the distance between the slits (i.e., the pore diameter) and the adsorption molecular weight can be obtained. This method is applicable to the case where the distance between the slits; i.e., the pore diameter is sufficiently small, and thus this is used for analysis of a pore distribution of a relatively small diameter of several nanometers or less. Details for the HK method are described in Horvath-Kawazoe, J. Chem. Eng. Jpn., 16, 470 (1983) as well.

<BET Specific Surface Area>

The BET specific surface area of the porous carbon material is not particularly limited and may be appropriately selected depending on the intended purpose. The BET specific surface area is preferably 500 m²/g or more but 2,000 m²/g or less, more preferably 700 m²/g or more but 1,800 m²/g or less, particularly preferably 800 m²/g or more but 1,500 m²/g or less.

[Specific Measurement Methods for Mesopore Volume, Micropore Volume, and BET Specific Surface Area]

Thirty milligrams of the porous carbon material is provided. The 3FLEX which is set to the conditions to measure in a relative pressure (P/P0) of 0.0000001 to 0.995 can be used to measure the mesopore volume, the micropore volume, and the BET specific surface area.

<Raw Material of Porous Carbon Material>

A raw material of the porous carbon material is preferably a plant-derived material. That is, the porous carbon material is preferably derived from a plant. When the raw material is plant-derived, a value of the mesopore volume and the above ratio are easily adjusted to the desired values described above. The plant-derived material is also advantageous in terms of a low environmental loading.

The plant-derived material is not particularly limited and may be appropriately selected depending on the intended purpose. Examples thereof include chaff or straw of rice, barley, wheat, rye, Japanese millet, and millet. Alternatively, reed or wakame stem may be used. Additional examples thereof include vascular plants living on the ground, pteridophyte, bryophyte, algae, and seaweeds. Note that, these materials may be used as the raw material alone or in a mixture of a plurality of them. A shape or form of the plant-derived material is also not particularly limited. For example, the chaff or straw may be used as it is or subjected to drying treatment. Moreover, those which have been subjected to various treatments such as fermentation treatment, roast treatment, and extraction treatment in food and drink processing such as beer, wines, and spirits may be used. In particular, in terms of attempting to recycle industrial wastes, straw and chaff which have been processed, e.g., thrashed are preferably used. These straw and chaff which have been processed can be abundantly and easily available from, for example, agricultural cooperatives, brewing manufactures, and food companies.

Applications of the porous carbon material are not particularly limited and may be appropriately selected depending on the intended purpose. Examples thereof include an adsorbent and a catalyst carrier. Among them, the porous carbon material can be suitably used as a catalyst carrier.

A method for producing the porous carbon material is not particularly limited and may be appropriately selected depending on the intended purpose, but is preferably the below-described method for producing a porous carbon material.

(Method for Producing Porous Carbon Material)

One example of the method for producing the porous carbon material of the present invention removes, from a raw material containing a silicon component, the silicon component by an acid treatment or an alkali treatment, and then performing a carbonization treatment. That is, the one example of the method for producing the porous carbon material includes a silicon-component-removal treatment and a carbonization treatment in this order.

Another example of the method for producing the porous carbon material of the present invention performs a carbonization treatment on a raw material containing a silicon component, then removes the silicon component from an obtained carbonized product by an acid treatment or an alkali treatment, and then performs an activation treatment. That is, the another example of the method for producing the porous carbon material includes a carbonization treatment, a silicon-component-removal treatment, and an activation treatment in this order.

The method for producing the porous carbon material of the present invention includes, a carbonization treatment, an activation treatment, and a silicon-component-removal treatment, and a heat treatment, and if necessary further includes other treatments.

The method for producing the porous carbon material is a method for producing the porous carbon material of the present invention.

<Silicon-Component-Removal Treatment>

The silicon-component-removal treatment is not particularly limited and may be appropriately selected depending on the intended purpose so long as it is a treatment of removing, from a raw material containing a silicon component or a carbonized product containing a silicon component after the carbonization treatment, the silicon component by an acid treatment or an alkali treatment. Examples thereof include a method of immersing the raw material or the carbonized product in an acid aqueous solution or an alkali aqueous solution.

The silicon-component-removal treatment makes it easier to increase the ratio in the carbonization treatment and the activation treatment.

<Carbonization Treatment>

The carbonization treatment is not particularly limited and may be appropriately selected depending on the intended purpose so long as it is a treatment of carbonizing (charring) a raw material, or a raw material subjected to the silicon-component-removal treatment, to obtain a carbonized product (carbonaceous material).

The carbonization (charring) generally means that an organic material (for example, plant-derived material in the present invention) is converted into a carbonaceous material through a heat treatment (e.g., see JIS M0104-1984). Note that, examples of an atmosphere under which the charring takes place include an oxygen-blocked atmosphere, in particular, a vacuum atmosphere and an inert gas atmosphere such as a nitrogen gas and an argon gas. A heating rate to reach a charring temperature may be 1° C./min or more, preferably 3° C./min or more, more preferably 5° C./min or more under such an atmosphere. The upper limit of a charring to time may include but not limited to 10 hours, preferably 7 hours, more preferably 5 hours. The lower limit of the charring time may be a time during which the raw material is surely charred.

The temperature of the carbonization treatment is not particularly limited and may be appropriately selected depending on the intended purpose. It is preferably 600° C. or higher, more preferably 600° C. or higher but 1,000° C. or lower.

<Activation Treatment>

The activation treatment is not particularly limited and may be appropriately selected depending on the intended purpose so long as it is a treatment of activating the carbonized product. Examples thereof include a gas activation method and a chemical activation method.

The activation as used herein means developing a pore structure in a carbonaceous material and adding pores to the carbonaceous material.

The gas activation method is a method in which the carbonized product is heated under a gas atmosphere using, as an activator, oxygen, water vapor, carbon dioxide, air, etc. at, for example, 700° C. or higher but 1,000° C. or lower for from several ten minutes to several hours to thereby develop a fine structure by a volatile component or a carbon molecule in the carbonized product. Note that, a heating temperature may be appropriately selected depending on a kind of the plant-derived material, and a kind and a concentration of the gas, but is preferably 850° C. or higher but 1,000° C. or lower.

The chemical activation method is a method in which the carbonized product is activated using, for example, zinc chloride, iron chloride, calcium phosphate, calcium hydroxide, magnesium carbonate, potassium carbonate, and sulfuric acid instead of oxygen or water vapor used in the gas activation method, washed with hydrochloric acid, pH-adjusted with an alkaline aqueous solution, and dried.

The time of the activation treatment is not particularly limited and may be appropriately selected depending on the intended purpose. It is preferably 0.5 hours or more but 20 hours or less, more preferably 1 hour or more but 10 hours or less.

In order to increase the ratio in the porous carbon material, it is also effective to extend the activation time.

<Heat Treatment>

The heat treatment is not particularly limited and may be appropriately selected depending on the intended purpose so long as it is a treatment of heating the carbonized product after the activation treatment. This treatment can increase the carbon density of the carbonized product, and can increase the electrical conductivity of the porous carbon material produced.

The temperature of the heat treatment is not particularly limited and may be appropriately selected depending on the intended purpose. It is preferably 1,200° C. or higher, preferably 1,200° C. or higher but 2,800° C. or lower, more preferably 1,200° C. or higher but 2,700° C. or lower, particularly preferably 1,200° C. or higher but 2,500° C. or lower.

The time of the heat treatment is not particularly limited and may be appropriately selected depending on the intended purpose. It is preferably 1 hour or more but 24 hours or less, more preferably 5 hours or more but 15 hours or less.

The heat treatment is preferably performed in the presence of a reducing gas to decrease the load on a furnace. Examples of the reducing gas include hydrogen gas, carbon monoxide gas, and vapor of organic matter (e.g., methane gas).

The reducing gas is preferably used together with an inert gas. Examples of the inert gas include nitrogen gas, helium gas, and argon gas.

One example of the method for producing the porous carbon material will be described with reference to FIG. 1.

FIG. 1 is a flowchart of one example of the method for producing the porous carbon material.

First, a plant serving as a raw material is provided (S1). The plant contains a silicon component.

Subsequently, the raw material is subjected to the silicon-component-removal treatment with an alkali, to remove the silicon component from the raw material (S2).

Subsequently, the raw material from which the silicon component has been removed is subjected to the carbonization treatment (S3). The carbonization treatment can provide a carbonized product.

Subsequently, the obtained carbonized product is subjected to the activation treatment (S4). The activation treatment develops a pore structure in the carbonized product.

Subsequently, the carbonized product after the activation treatment is subjected to the heat treatment (S5). The heat treatment increases the carbon density of the carbonized product and increases the electrical conductivity.

Through the above procedure, the porous carbon material is obtained.

Another example of the method for producing the porous carbon material will be described with reference to FIG. 2.

Figure 2:
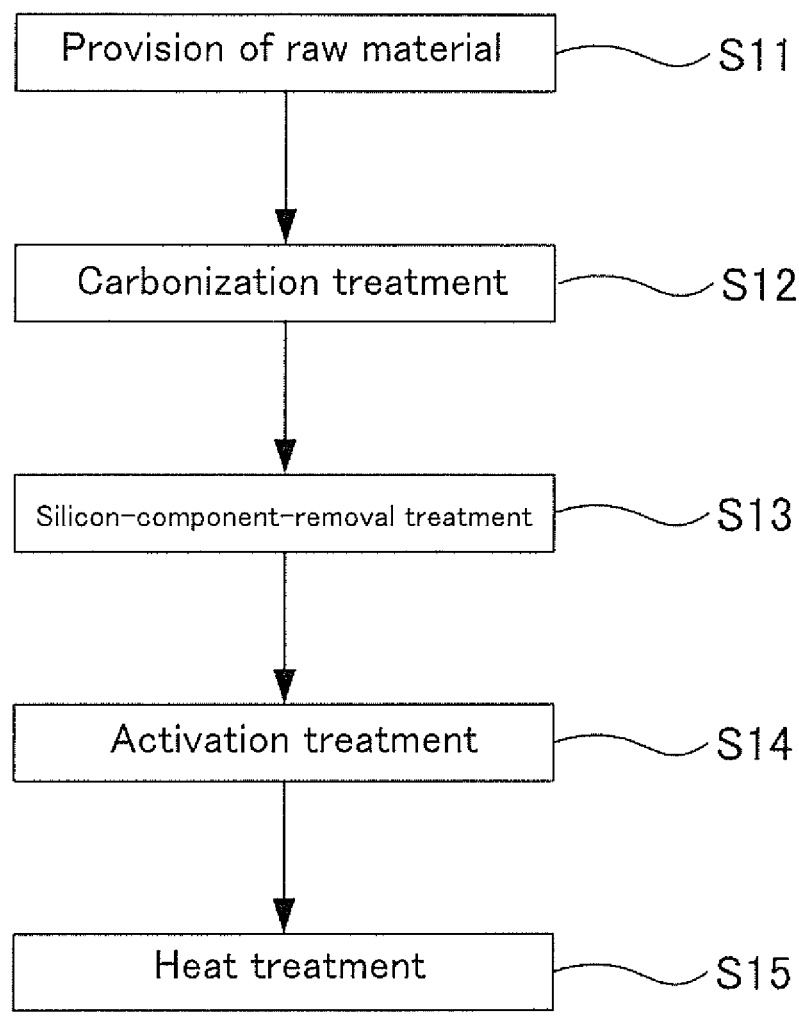
FIG. 2 is a flowchart of another example of a method for producing a porous carbon material.

FIG. 2 is a flowchart of one example of the method for producing the porous carbon material.

First, a plant serving as a raw material is provided (S11). The plant contains a silicon component.

Subsequently, the raw material is subjected to the carbonization treatment (S12). The carbonization treatment can provide a carbonized product.

Subsequently, the obtained carbonized product is subjected to the silicon-component-removal treatment with an alkali, to remove the silicon component from the carbonized product (S13).

Subsequently, the carbonized product from which the silicon component has been removed is subjected to the activation treatment (S14). The activation treatment develops a pore structure in the carbonized product.

Subsequently, the carbonized product after the activation treatment is subjected to the heat treatment (S15). The heat treatment increases the carbon density of the carbonized product and increases the electrical conductivity.

Through the above procedure, the porous carbon material is obtained.

(Synthesis Reaction Catalyst)

A synthesis reaction catalyst of the present invention includes: the porous carbon material of the present invention; and a metal or a metal compound carried on the porous carbon material; and if necessary further includes other components.

The metal is not particularly limited and may be appropriately selected depending on the intended purpose so long as it is a catalytic active component. Examples thereof include platinum group elements (platinum, iridium, osmium, ruthenium, rhodium, and palladium), rhenium, gold, and silver.

The metal compound is not particularly limited and may be appropriately selected depending on the intended purpose so long as it is a catalytic active component. Examples thereof include alloys of the metals mentioned above.

Among them, the metal or the metal compound is preferably palladium in terms of cost and availability.

Examples of a method of carrying the metal or the metal compound on the porous carbon material include the following methods:

(1) a method in which the porous carbon material serving as the catalyst carrier is dispersed in a solution of the metal serving as the catalytic active component, and a reducing agent is further added to reduce metal ions in the solution, to thereby deposit the metal on the porous carbon material serving as the catalyst carrier; and (2) a method in which a solution of the metal serving as the catalytic active component, the solution containing the porous carbon material serving as the catalyst carrier dispersed, is stirred with heating to deposit the catalytic active component on the catalyst carrier, and then filtration, washing, drying, and the like are appropriately performed, followed by a reducing treatment with hydrogen gas.

The ratio between the porous carbon material and the metal or the metal compound in the synthesis reaction catalyst is not particularly limited and may be appropriately selected depending on the intended purpose.

(Method for Synthesizing Compound)

A method for synthesizing a compound includes at least a reduction step; and if necessary further include other steps.

<Reduction Step>

The reduction step is not particularly limited and may be appropriately selected depending on the intended purpose so long as it is a step of reducing a compound.

The compound is not particularly limited and may be appropriately selected depending on the intended purpose so long as it is a compound having a reducible bond or group. Examples thereof include compounds having a reducible double bond or triple bond.

Examples of the reduction include reduction of a double bond to a single bond and reduction of a triple bond to a double bond or a single bond.

Examples of the compound include a compound having an acetylene group (—C≡C—). Examples of the compound having an acetylene group include diphenylacetylene.

In the method for synthesizing the compound, when diphenylacetylene is reduced, for example, bibenzyl is obtained.

The amount of the synthesis reaction catalyst used in the method for synthesizing the compound is not particularly limited and may be appropriately selected depending on the intended purpose. It is preferably 0.5 parts by mass or more but 5.0 parts by mass or less, more preferably 1.0 part by mass or more but 3.0 parts by mass or less, with respect to 100 parts by mass of the compound.

In the method for synthesizing the compound, heating may be performed or the reaction may be performed at ambient temperature.

The method for synthesizing the compound is preferably performed in the presence of a reducing gas. Examples of the reducing gas include hydrogen gas, carbon monoxide gas, and vapor of organic matter (e.g., methane gas).

EXAMPLES

Examples of the present invention will now be described, but the present invention is not limited to these Examples.

<Raw Material>

Chaff manufactured in Miyagi prefecture was used as the raw material.

<Alkali Treatment>

The alkali treatment (the silicon-component-removal treatment) for removing a silicon component was performed by immersing the chaff in an aqueous solution containing sodium hydroxide in an amount of 5.3% by mass at 90° C. for 14 hours.

<Carbonization Treatment>

The carbonization treatment was performed in a carbonization furnace under a nitrogen atmosphere ($N_2$=30 L/min) at 600° C. for 3 hours.

<Activation Treatment>

The activation treatment was performed at 950° C. for a predetermined time with water vapor under nitrogen bubbling ($N_2$=5 L/min) conditions using a Rotary kiln.

<Heat Treatment>

The heat treatment was performed at a predetermined temperature for 10 hours under supply of hydrogen/nitrogen mixed gas (4% by mass of hydrogen relative to nitrogen) (30 L/min).

Comparative Examples 1 to 4

The alkali treatment, the carbonization treatment, and the activation treatment were performed on the chaff in this order under the conditions presented in Table 1, to obtain porous carbon materials.

Examples 1 to 4

The alkali treatment, the carbonization treatment, and the activation treatment were performed on the chaff in this order under the conditions presented in Table 1, to obtain porous carbon materials.

The obtained porous carbon materials were subjected to the following evaluations. The results are presented in Table 2.

<Half Width>

The measurement of the half width (2θ) of (10x) (38° to 49°) by X-ray diffraction was performed by PHILIPS X'Pert available from PANalytical Co.

Figure 3:
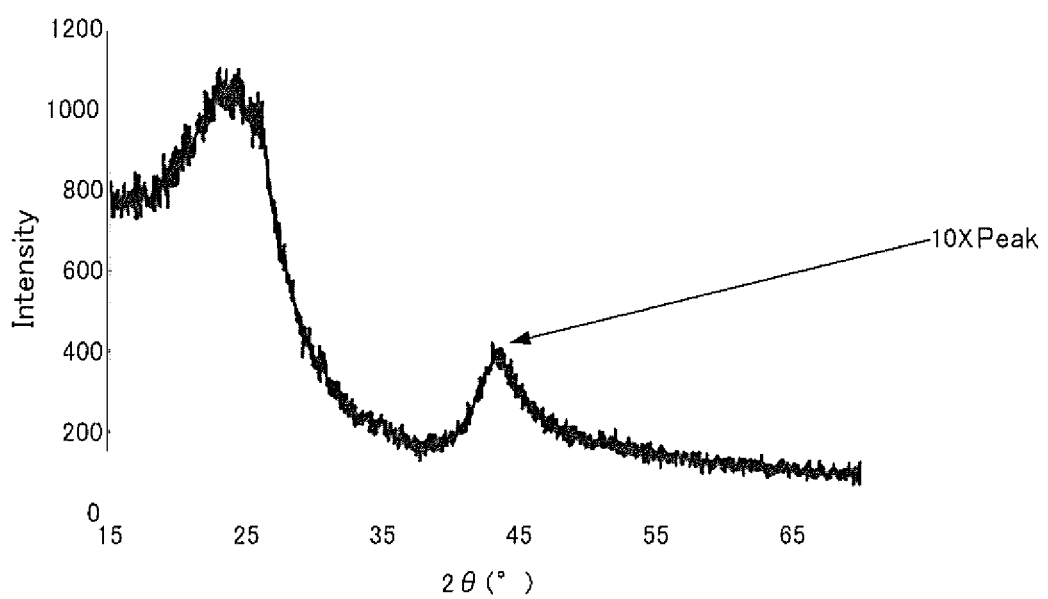
FIG. 3 is a graph depicting X-ray diffraction results in Example 2.

The X-ray diffraction results of the porous carbon material of Example 2 are presented in FIG. 3.

<BET Specific Surface Area, Micropore Volume, and Mesopore Volume>

The measurement of the BET specific surface area, the micropore volume, and the mesopore volume was performed using a multi-analyte high-performance specific surface area/pore distribution measuring device 3FLEX available from Micromeritics Corporation.

<Catalytic Performance>
<<Production of Palladium Carbon Catalyst>>

The porous carbon material was immersed in a hydrochloric acid solution adjusted so that a Pd metal would be 5% by mass with respect to 1 g of the porous carbon material. Thereafter, the resultant was dried under reduced pressure for 2 hours at 100° C. Further, a reduction treatment was performed for 3 hours at 400° C. in an atmosphere of hydrogen-containing gas. As a result, a palladium carbon catalyst carrying palladium on the porous carbon material was obtained.

<<Synthesis of Bibenzyl>>

The following components of the following amounts were charged to a 10-ml test tube, and the resultant mixture was stirred at 500 rpm while supplying hydrogen gas with a balloon, to thereby perform hydrogenation reaction for 1 hour.

The main product was bibenzyl, and the reaction yield was calculated from the amount of diphenylacetylene charged. The reaction yield was obtained using Agilent 6890N/5975MSD.

[Components and Amounts Thereof]
Diphenylacetylene: 89.1 mg
The above palladium carbon catalyst: 1.6 mg
Heavy methanol serving as a solvent: 1 ml The porous carbon materials produced in Examples 1 to 4 indicated excellent catalytic performance when formed into a catalyst as compared with the porous carbon materials produced in Comparative Examples 1 to 4.

That is, in the case where the half width ($2\theta$) of (10×) (38° to 49°) by X-ray diffraction was higher than 4.2°, even if the mesopore volume/micropore volume ratio was 1.20 or more, the reaction yield of bibenzyl was low (Comparative Examples 2 and 3). Also in the case where the mesopore volume/micropore volume ratio was less than 1.20, the reaction yield of bibenzyl was low (Comparative Examples 1 and 4).

Meanwhile, when the half width ($2\theta$) of (10×) (38° to 49°) by X-ray diffraction was 4.2° or less and the mesopore volume/micropore volume ratio was 1.20 or more, the reaction yield of bibenzyl was good; i.e., 80% or more.

INDUSTRIAL APPLICABILITY

The porous carbon material of the present invention can be used for, for example, catalyst carriers.

The invention claimed is:
1. A porous carbon material,
wherein a half width ($2\theta$) of a diffraction peak (10×) (38° to 49°) by X-ray diffraction is 4.2° or less, wherein 10× means a pseudo peak observed in the vicinity of the 101 plane in graphite, and

TABLE 1

| | | | Production method | | | | | |
|---|---|---|---|---|---|---|---|---|
| | | | Carbonization treatment | | Activation treatment | | Heat treatment | |
| Items | Raw material | Alkali treatment | Temp. °C. | Time Hr | Temp. °C. | Time Hr | Temp. °C. | Time Hr |
| Comp. Ex. 1 | Chaff | Performed | 600 | 3 | 950 | 3 | — | — |
| Ex. 1 | | | | | | 3 | 1200 | 10 |
| Ex. 2 | | | | | | 3 | 1500 | 10 |
| Comp. Ex. 2 | | | | | | 6 | — | — |
| Ex. 3 | | | | | | 6 | 1500 | 10 |
| Comp. Ex. 3 | | | | | | 8 | — | — |
| Ex. 4 | | | | | | 8 | 1500 | 10 |
| Comp. Ex. 4 | | | | | | 3 | 1200 | 5 |

TABLE 2

| | (10X) Half width (°) 38° to 49° | BET specific surface area (m2/g) | Micropore volume (cm3/g) | Mesopore volume (cm3/g) | Mesopore volume/Micropore volume ratio | Catalytic performance Reaction yield (%) |
|---|---|---|---|---|---|---|
| Comp. Ex. 1 | 4.7 | 1002 | 0.43 | 0.47 | 1.09 | 65.7 |
| Ex. 1 | 4.0 | 936 | 0.40 | 0.49 | 1.23 | 80.2 |
| Ex. 2 | 3.7 | 820 | 0.36 | 0.50 | 1.39 | 84.1 |
| Comp. Ex. 2 | 4.5 | 1420 | 0.61 | 0.82 | 1.34 | 61.6 |
| Ex. 3 | 3.7 | 1117 | 0.49 | 0.75 | 1.53 | 86.9 |
| Comp. Ex. 3 | 4.4 | 1660 | 0.72 | 1.11 | 1.54 | 60.1 |
| Ex. 4 | 3.7 | 1429 | 0.65 | 1.13 | 1.74 | 80.3 |
| Comp. Ex. 4 | 4.1 | 951 | 0.42 | 0.47 | 1.12 | 67.2 | wherein a ratio (mesopore volume/micropore volume) of a mesopore volume (cm$^3$/g) measured by a BJH method to a micropore volume (cm$^3$/g) measured by a HK method is 1.20 or more, but 2.00 or less.

2. The porous carbon material according to claim 1, wherein the porous carbon material is derived from a plant.

3. The porous carbon material according to claim 1, wherein the porous carbon material is derived from chaff.

4. The porous carbon material according to claim 1, wherein the porous carbon material is a carrier for a catalyst.

5. A method for producing the porous carbon material according to claim 1, the method comprising:
removing, from a raw material containing a silicon component, the silicon component by an acid treatment or an alkali treatment, and then performing a carbonization treatment.

6. The method for producing the porous carbon material according to claim 5, wherein an activation treatment is performed after the carbonization treatment.

7. The method for producing the porous carbon material according to claim 6, wherein a heat treatment is performed after the activation treatment.

8. The method for producing the porous carbon material according to claim 7, wherein a temperature of the heat treatment is 1,200° C. or higher.

9. The method for producing the porous carbon material according to claim 5, wherein a temperature of the carbonization treatment is 600° C. or higher.

10. A method for producing the porous carbon material according to claim 1, the method comprising:
performing a carbonization treatment on a raw material containing a silicon component, then removing the silicon component from an obtained carbonized product by an acid treatment or an alkali treatment, and then performing an activation treatment.

11. The method for producing the porous carbon material according to claim 10, wherein a heat treatment is performed after the activation treatment.

12. The method for producing the porous carbon material according to claim 11, wherein a temperature of the heat treatment is 1,200° C. or higher.

13. The method for producing the porous carbon material according to claim 10, wherein a temperature of the carbonization treatment is 600° C. or higher.

14. A synthesis reaction catalyst comprising:
the porous carbon material according to claim 1; and
a metal or a metal compound carried on the porous carbon material.

15. The synthesis reaction catalyst according to claim 14, wherein the metal or the metal compound palladium.

16. A porous carbon material,
wherein the porous carbon material is subjected to heat treatment at a temperature of 1,200° C. or higher,
wherein the porous carbon material exhibits the following properties after heat treatment:
(a) a half width (2θ) of a diffraction peak (10×) (38° to 49°) by X-ray diffraction is 4.2° or less, wherein 10× means a pseudo peak observed in the vicinity of the 101 plane graphite, and
(b) a ratio (mesopore volume/micropore volume) of a mesopore volume (cm$^3$/g) measured by a Bill method to a micropore volume (cm$^3$/g) measured by a HK method is 1.20 or more, but 2.00 or less.

* * * * *